(12) United States Patent
Albright et al.

(10) Patent No.: US 10,852,282 B2
(45) Date of Patent: Dec. 1, 2020

(54) SYSTEM AND METHOD FOR DETERMINING A CONCENTRATION OF A CONSTITUENT GAS IN A GAS STREAM USING PRESSURE MEASUREMENTS

(71) Applicant: Hitachi Metals, Ltd., Tokyo (JP)

(72) Inventors: Patrick Albright, Wellington, CO (US); Ryan Johnson, Fort Collins, CO (US)

(73) Assignee: Hitachi Metals, Ltd., Tokyo (JP)

( * ) Notice: Subject to any disclaimer, the term of this patent is extended or adjusted under 35 U.S.C. 154(b) by 252 days.

(21) Appl. No.: 15/378,833

(22) Filed: Dec. 14, 2016

(65) Prior Publication Data

US 2017/0168036 A1 Jun. 15, 2017

Related U.S. Application Data

(60) Provisional application No. 62/266,848, filed on Dec. 14, 2015.

(51) Int. Cl.

| | |
|---|---|
| *C23C 16/455* | (2006.01) |
| *G01N 33/00* | (2006.01) |
| *G01F 1/34* | (2006.01) |
| *G01F 1/76* | (2006.01) |
| *C23C 16/448* | (2006.01) |

(52) U.S. Cl.
CPC ..... *G01N 33/0073* (2013.01); *C23C 16/4482* (2013.01); *C23C 16/455* (2013.01); *G01F 1/34* (2013.01); *G01F 1/76* (2013.01); *G01N 33/0011* (2013.01)

(58) Field of Classification Search
CPC ............ G01N 33/0073; G01N 33/0004; C23C 16/4482
See application file for complete search history.

(56) References Cited

U.S. PATENT DOCUMENTS

| | | | |
|---|---|---|---|
| 7,651,263 B2 | 1/2010 | Zolock et al. | |
| 8,499,786 B2 | 8/2013 | Zolock et al. | |
| 8,504,311 B2 | 8/2013 | Smirnov et al. | |
| 2011/0247390 A1 | 10/2011 | Smirnov et al. | |
| 2011/0247696 A1 | 10/2011 | Zolock et al. | |
| 2014/0299206 A1* | 10/2014 | Nagase | C23C 16/4482 137/551 |
| 2017/0101715 A1* | 4/2017 | Nishizato | C23C 16/52 |

* cited by examiner

*Primary Examiner* — Herbert K Roberts
(74) *Attorney, Agent, or Firm* — Neugeboren O'Dowd PC

(57) ABSTRACT

Systems and methods for determining a concentration of a constituent gas in a gas stream using pressure measurements are disclosed. A method may include a vaporizer receiving a carrier gas and a source material, and vaporizing the source material in the vaporizer to produce a gas stream including the carrier gas and the constituent vapor. Then, a pressure of a chamber of the vaporizer is obtained, a mass flow rate of the gas stream is measured, and a temperature of the chamber of the vaporizer is measured. A constituent-vapor-concentration signal indicative of the concentration the constituent vapor in the gas stream is then generated. The mass flow rate of the constituent vapor may be determined using the concentration of the constituent vapor, and the mass flow rate of the constituent vapor may then be controlled using the determined mass flow rate of the constituent vapor.

6 Claims, 6 Drawing Sheets

SYSTEM AND METHOD FOR DETERMINING A CONCENTRATION OF A CONSTITUENT GAS IN A GAS STREAM USING PRESSURE MEASUREMENTS

CLAIM OF PRIORITY UNDER 35 U.S.C. § 119

The present Application for Patent claims priority to Provisional Application No. 62/266,848 entitled "SYSTEM AND METHOD FOR DETERMINING A CONCENTRATION OF A CONSTITUENT GAS IN A GAS STREAM USING PRESSURE MEASUREMENTS" filed Dec. 14, 2015, and assigned to the assignee hereof and hereby expressly incorporated by reference herein.

FIELD OF THE INVENTION

The present invention relates to systems and methods for mass flow measurement and control. In particular, but not by way of limitation, the present invention relates to systems and methods for measuring a concentration of a gas species in a flow of gas and control based upon the same.

BACKGROUND OF THE INVENTION

Several different types of processing operations (e.g., thin film deposition operations) rely on a precise delivery of a gas to a processing environment (e.g., a plasma processing environment). As the dimensions of the structures that are fabricated continue to diminish in size, the precision of the mass flow rate of the gas continues to increase in importance.

One approach to delivering a constituent vapor species to a process environment includes using a vaporizer to vaporize a source substance into a specific type of gas that is desired in the process environment. A pressurized carrier gas is then utilized to force the constituent vapor to the process environment, but mixing the carrier gas with the constituent vapor results in two known gases in the gas stream, and problematically, the concentration of the constituent vapor is difficult to determine.

SUMMARY

According to an aspect, a mass flow control system is disclosed. The mass flow control system includes a vaporizer disposed to receive a carrier gas and a source material to be vaporized, and the vaporizer is configured to vaporize the source material to provide a constituent vapor along with the carrier gas as a gas stream. The system also includes an upstream pressure sensor coupled to an input to the vaporizer, wherein the upstream pressure sensor is configured to sense a pressure of the carrier gas and provide an upstream pressure signal indicative of the pressure of the carrier gas.

A downstream pressure sensor of the mass flow control system is coupled to an output of the vaporizer, and the downstream pressure sensor is configured to sense a pressure of the gas stream at an output of the vaporizer and provide a downstream pressure signal. A mass flow meter is coupled to the output of the vaporizer, and the mass flow meter is configured to provide a gas-stream-flow-rate signal indicative of a mass flow rate of the gas stream. A temperature sensor is thermally coupled to the vaporizer, and the temperature sensor is configured to provide a vaporizer-temperature signal indicative of a temperature of the chamber of the vaporizer.

The mass flow control system also includes a constituent vapor meter configured to provide a constituent-vapor-concentration signal using the upstream pressure signal, the downstream pressure signal, the gas-stream-flow-rate signal, the vaporizer-temperature signal, and information about the carrier gas and the constituent vapor, wherein the constituent-vapor-concentration signal is indicative of a concentration of the constituent vapor in the gas stream. A constituent-vapor mass flow meter is configured to provide a constituent-vapor-mass-flow-rate signal by multiplying the concentration of the constituent vapor in the gas stream by the mass flow rate of the gas stream, wherein the constituent-vapor-mass-flow-rate signal is indicative of a mass flow rate of the constituent vapor. A mass flow control module is included in the system to adjust a mass flow rate of the gas stream until the mass flow rate of the constituent vapor equals a constituent-vapor-setpoint.

According to another aspect, a mass flow control system includes a vaporizer disposed to receive a carrier gas and a source material to be vaporized, wherein the vaporizer is configured to vaporize the source material to provide a constituent vapor along with the carrier gas as a gas stream. The system also includes a vaporizer-pressure sensor coupled to the vaporizer, wherein the vaporizer-pressure sensor is configured to sense a pressure of a chamber of the vaporizer and provide a vaporizer-pressure signal indicative of the pressure of a chamber of the vaporizer. A mass flow meter is coupled to the output of the vaporizer, and the mass flow meter is configured to provide a gas-stream-flow-rate signal indicative of a mass flow rate of the gas stream. A temperature sensor is thermally coupled to the vaporizer, wherein the temperature sensor is configured to provide a vaporizer-temperature signal indicative of a temperature of a chamber of the vaporizer. A constituent vapor meter is included and is configured to provide a constituent-vapor-concentration signal using the vaporizer-pressure signal, the gas-stream-flow-rate signal, the vaporizer-temperature signal, and information about the carrier gas and the constituent vapor, wherein the constituent-vapor-concentration signal is indicative of a concentration of the constituent vapor in the gas stream. A constituent-vapor mass flow meter is configured to provide a constituent-vapor-mass-flow-rate signal by multiplying the concentration of the constituent vapor in the gas stream by the mass flow rate of the gas stream, wherein the constituent-vapor-mass-flow-rate signal is indicative of a mass flow rate of the constituent vapor, and a mass flow control module is configured to adjust a mass flow rate of the gas stream until the mass flow rate of the constituent vapor equals a constituent-vapor-setpoint.

According to yet another aspect, a mass flow controller includes a conduit to receive a gas stream including a carrier gas and a constituent vapor. The mass flow controller includes a mass flow meter disposed to receive the gas stream from the conduit and provide a gas-stream-flow-rate signal indicative of a mass flow rate of the gas stream. A constituent vapor meter configured to provide a constituent-vapor-concentration signal using an upstream pressure signal, a downstream pressure signal, the gas-stream-flow-rate signal, a vaporizer-temperature signal, and information about the carrier gas and the constituent vapor, wherein the constituent-vapor-concentration signal is indicative of a concentration of the constituent vapor in the gas stream. A constituent-vapor mass flow meter is configured to provide a constituent-vapor-mass-flow-rate signal by multiplying the concentration of the constituent vapor in the gas stream by the mass flow rate of the gas stream, wherein the constituent-vapor-mass-flow-rate signal is indicative of a mass flow rate of the constituent vapor. A control valve is coupled to the conduit to control a mass flow rate of the gas stream, and a controller is disposed to receive the constituent-vapor-mass-flow-rate signal and adjust the control valve so the constituent-vapor-mass-flow-rate signal equals a constituent-vapor-setpoint signal.

Another aspect of the disclosure includes a mass flow controller that includes a conduit to receive a gas stream including a carrier gas and a constituent vapor. The mass flow controller also includes a mass flow meter disposed to receive the gas stream from the conduit and provide a gas-stream-flow-rate signal indicative of a mass flow rate of the gas stream. A constituent vapor meter is configured to provide a constituent-vapor-concentration signal using a vaporizer-pressure signal, the gas-stream-flow-rate signal, a vaporizer-temperature signal, and information about the carrier gas and the constituent vapor, wherein the constituent-vapor-concentration signal is indicative of a concentration of the constituent vapor in the gas stream. A constituent-vapor mass flow meter is included to provide a constituent-vapor-mass-flow-rate signal by multiplying the concentration of the constituent vapor in the gas stream by the mass flow rate of the gas stream, wherein the constituent-vapor-mass-flow-rate signal is indicative of a mass flow rate of the constituent vapor. A control valve is coupled to the conduit to control a mass flow rate of the gas stream, and a controller is disposed to receive the constituent-vapor-mass-flow-rate signal and adjust the control valve so the constituent-vapor-mass-flow-rate signal equals a constituent-vapor-setpoint signal.

DETAILED DESCRIPTION

Figure 1A:
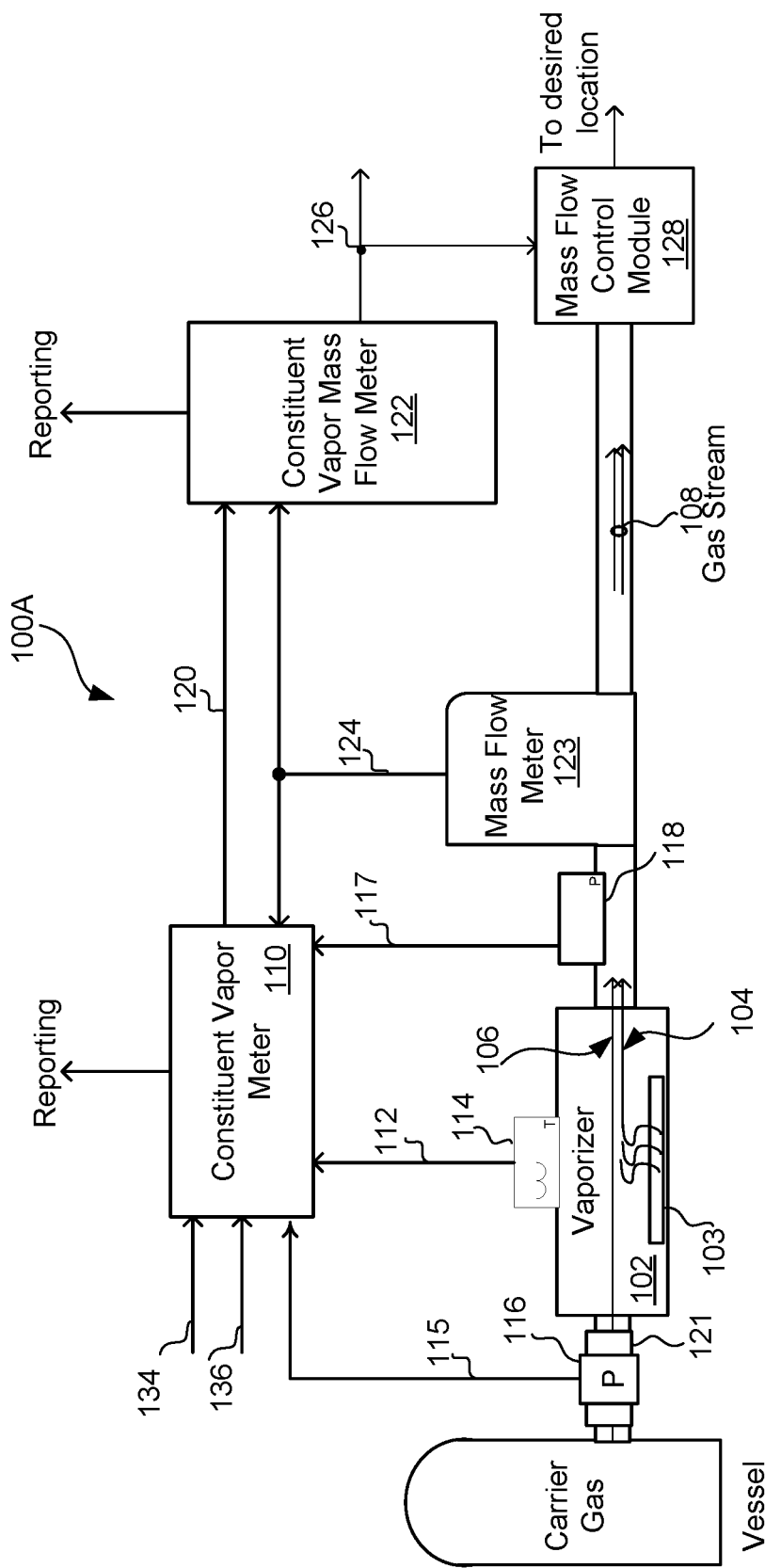
FIG. 1A is a block diagram depicting a mass flow control and gas concentration metering system.

Referring first to FIG. 1A, shown is a constituent vapor metering and control system 100A depicting several aspects of the present disclosure. As shown, a vaporizer 102 is utilized to vaporize a source material 103 into a constituent vapor 104, and a pressurized carrier gas 106 is employed to carry the constituent vapor 104 in a desired direction. As depicted, the carrier gas 106 mixes with the constituent vapor 104 to form a gas stream 108 that is provided to a desired location such as a plasma processing chamber (not shown). According to several aspects, a constituent vapor meter 110 provides a constituent-vapor-concentration signal 120 as an indication of the concentration of the constituent vapor 104 in the gas stream 108. The concentration of the constituent vapor 104 may be reported to an operator of the constituent vapor metering and control system 100A and/or the concentration of the constituent vapor 104 may be used to control a mass flow rate of the constituent vapor 104 as discussed in more detail further herein.

As depicted, the constituent vapor meter 110 receives a temperature signal 112 from a temperature sensor 114, an upstream pressure signal 115 from an upstream pressure sensor 116; a downstream pressure signal 117 from a downstream pressure sensor 118, and a gas-stream-flow-rate signal 124 (indicative of a mass flow rate of the gas stream 108) from a mass flow meter 123. In addition, the constituent vapor meter 110 may be configured to receive a constituent vapor signal 134 (that indicates a type of source material 103 being used, and hence, a type constituent vapor 104 being used) and a carrier gas signal 136 (that indicates a type of carrier gas 106 that is being used). As described further herein, the constituent vapor meter 110 is configured to generate the constituent-vapor-concentration signal 120 using the following as inputs: the upstream pressure signal 115, the downstream pressure signal 117, the gas-stream-flow-rate signal 124, the vaporizer-temperature signal 112, and information about the constituent vapor 104 and the carrier gas 106, wherein the constituent-vapor-concentration signal 120 is indicative of a concentration of the constituent vapor 104 in the gas stream 108.

As one of ordinary skill in the art will appreciate in view of this disclosure, the upstream pressure of the gas (e.g., upstream from the vaporizer 102) that is conveyed by the upstream pressure signal 115 and the downstream pressure of the gas stream 108 (e.g., at the inlet of the mass flow meter 123) conveyed by the downstream pressure signal 117 enable a pressure of a chamber of the vaporizer 102 to be calculated. A rate of vaporization of the source material 103 may be inferred from the pressure of the chamber of the vaporizer 102 because the rate of vaporization is inversely proportional to the pressure of the chamber of the vaporizer 102. In a variation of the embodiment depicted in FIG. 1A, a pressure of the chamber of the vaporizer 102 may be directly measured; thus removing the need for the upstream pressure sensor 116 and the downstream pressure sensor 118.

The temperature of the vaporizer 102 also affects a rate of vaporization of the source material 103. More specifically, the rate of vaporization of the source material 103 is directly proportional to temperature. Thus, the temperature signal 112 and pressure (inferred from the upstream pressure signal 115 and a downstream pressure signal 117) provide information about the rate of vaporization of the source material 103. The mass flow rate of the gas stream 108 (indicated by the gas-stream-flow-rate signal 124) may be used to determine a speed of the gas stream 108 through the vaporizer 102. The concentration of the constituent vapor 104 is inversely proportional to gas speed. And as one of ordinary skill in the art will appreciate in view of this disclosure, chemical properties of the carrier gas 106 and the constituent vapor 104 also affect the concentration of the constituent vapor 104 in the gas stream 108.

In many modes of operation, when a set point change occurs, a pressure of the gas stream 108 at the downstream pressure sensor 118 will also change due to resistance caused by the upstream gas plumbing between an upstream pressure regulator 121 and the downstream pressure sensor 118. In dynamic modes of operation with changing set points, the varying parameter values of pressure, temperature, and other conditions may be used to estimate a rate of vaporization of the material 103, and as a consequence, the constituent vapor meter 110 may determine the concentration of the constituent vapor 104 in the gas stream 108.

As depicted, a constituent-vapor mass flow meter 122 is disposed and configured to calculate a mass flow rate of the constituent vapor 104 using the constituent-vapor-concentration signal 120 and a measure of the mass flow rate of the gas stream (including the constituent vapor 104 and the carrier gas 106) as a whole. The constituent-vapor mass flow meter 122 may determine the mass flow rate of the constituent vapor 104 by multiplying the concentration of the constituent vapor 104 in the gas stream 108 by the mass flow rate of the gas stream 108. The mass flow rate of the constituent vapor 104 may be conveyed as a constituent-vapor-mass-flow-rate signal 126.

Also shown in FIG. 1A is a mass flow control module 128 that is coupled to the mass flow meter 123 downstream of the mass flow meter 123. The mass flow control module 128 is configured to adjust a mass flow rate of the gas stream 108 until the mass flow rate of the constituent vapor 104 equals a desired level, which may be set by a constituent-vapor setpoint.

Figure 1B:
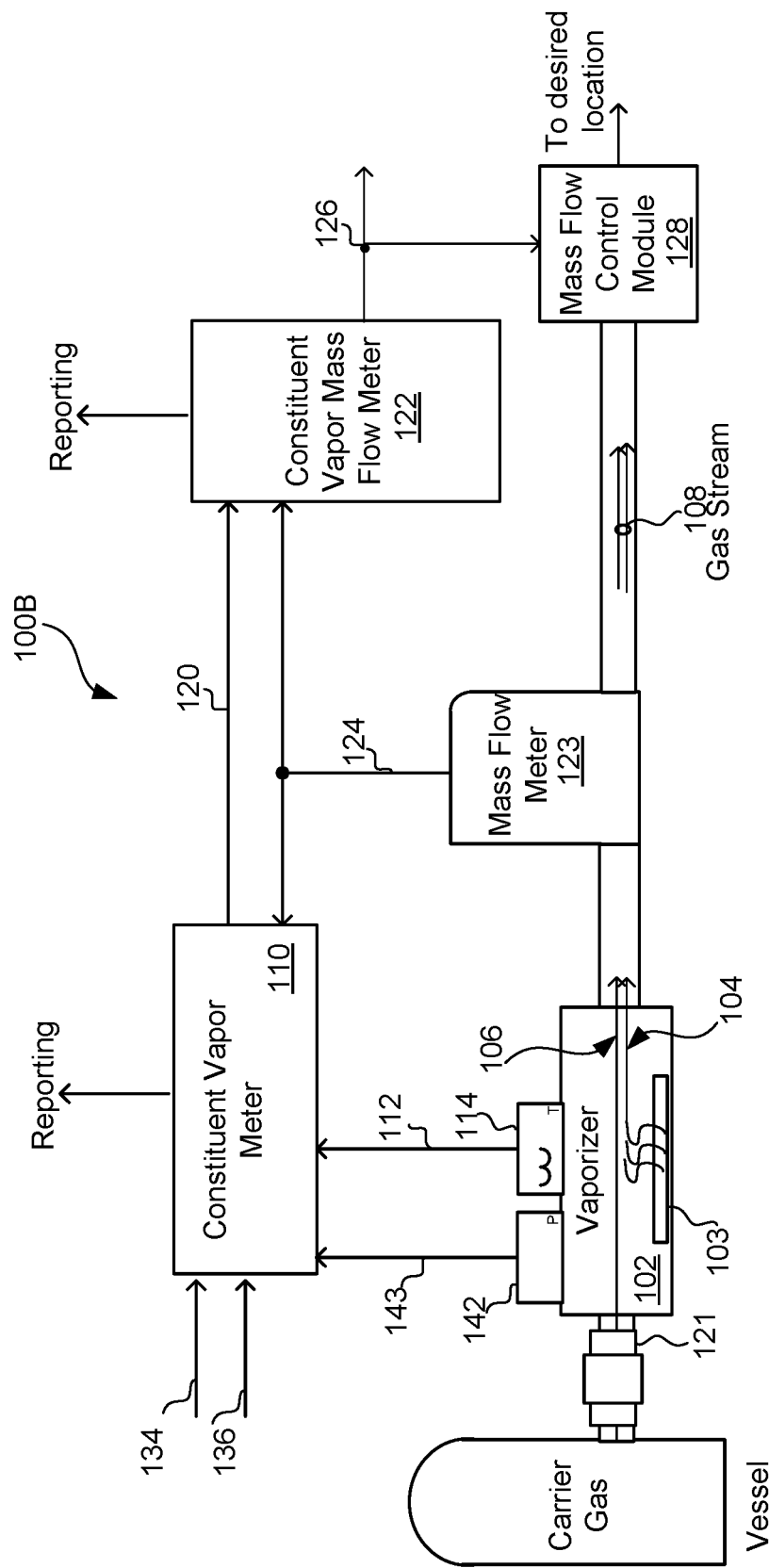
FIG. 1B is a block diagram depicting a mass flow control and gas concentration metering system.

Referring next to FIG. 1B, shown is a constituent vapor metering and control system 100B, which is a variation of the constituent vapor metering and control system 100A depicted in FIG. 1A. In this embodiment, the constituent vapor metering and control system 100B includes a vaporizer-pressure sensor 142 that is coupled to the vaporizer 102, and the vaporizer-pressure sensor 142 is configured to sense of a pressure of a chamber of the vaporizer 102 and provide a vaporizer-pressure signal 143 indicative of the pressure of a chamber of the vaporizer 102. The vaporizer-pressure sensor 142 provides (via the vaporizer-pressure signal 143) a direct measurement of the pressure of the chamber of the vaporizer 102; thus the constituent vapor meter 110 may generate the constituent-vapor-concentration signal 120 without either the upstream pressure signal 115 or the downstream pressure signal 117.

The depicted arrangement of components of the constituent vapor metering systems 100A, 100B is intended to convey several functional aspects, but the constituent vapor metering systems 100A, 100B may be realized in many different forms without departing from the scope of the invention. For example, the vaporizer 102 and all of the components downstream of the vaporizer 102 may be integrated into a unitary vaporizer unit that is configured to enable an operator to control and deliver a precise amount of the constituent vapor 104. Alternatively, all of the components downstream from the vaporizer 102 may be implemented as part of a mass flow controller.

Figure 2A:
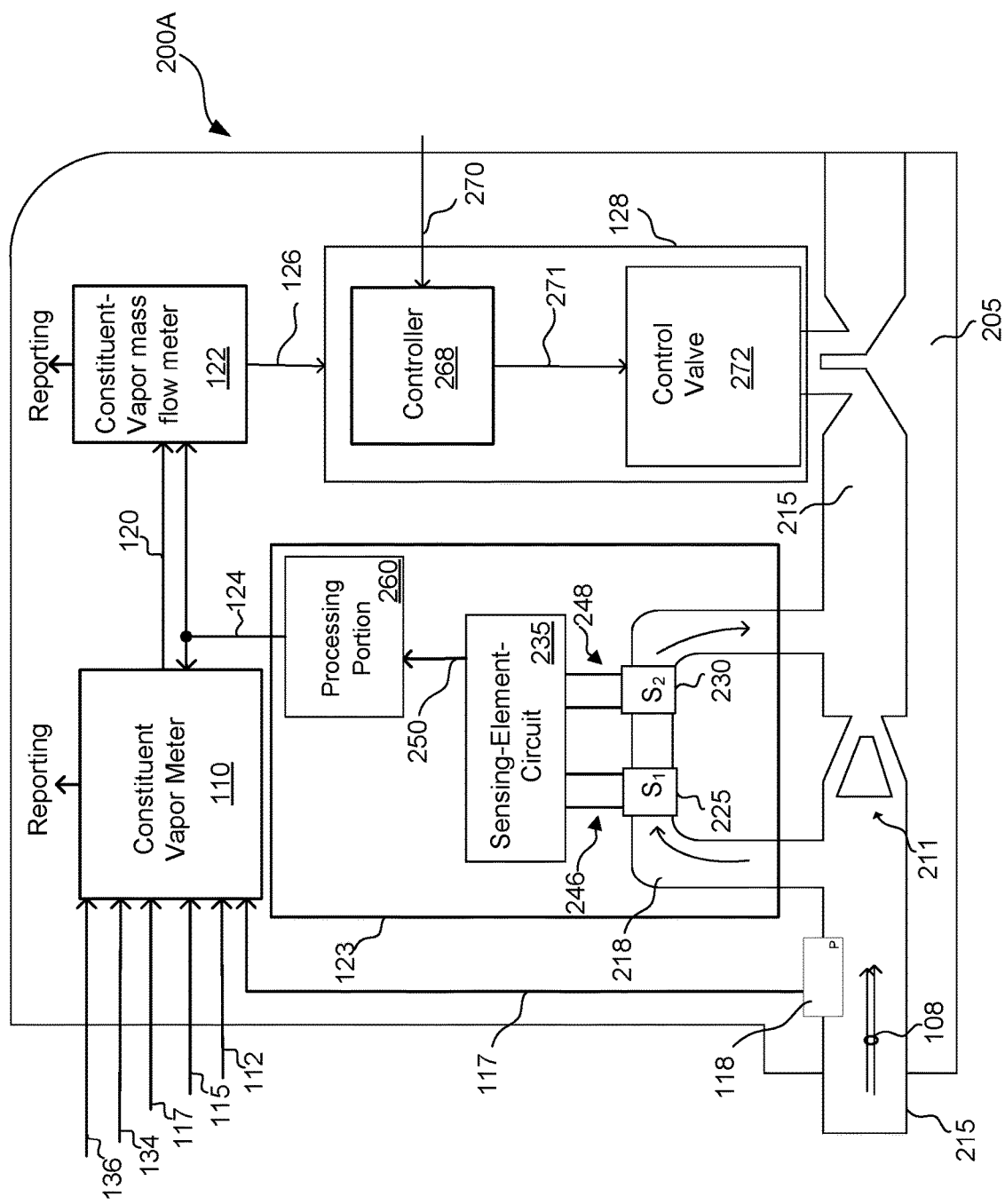
FIG. 2A is a block diagram depicting an embodiment of a mass flow controller.

Referring next to FIG. 2A, for example, shown is a functional block diagram of a mass flow controller (MFC) 200A in accordance with an illustrative embodiment of the invention. As shown, the constituent vapor meter 110, the downstream pressure sensor 118, the constituent-vapor mass flow meter 122, the mass flow meter 123, and the mass flow control module 128 are integrated into the MFC 200A. The illustrated arrangement of these components is logical and not meant to be an actual hardware diagram. Thus, portions of the components can be combined, further separated, deleted and/or supplemented in an actual implementation.

In the present embodiment, a base 205 of MFC 200A includes a bypass portion 211 through which the gas stream 108 flows. The bypass portion 111 directs a constant proportion of gas through main path 215 and sensor tube 218. As a consequence, the flow rate of the gas through the sensor tube 218 is indicative of the flow rate of the gas flowing through the main path 215 of the MFC 200A.

In this embodiment, the sensor tube 218 is a small bore tube that is part of the mass flow meter 123 of the MFC 200A. And as shown, sensing elements 225 and 230 are coupled to (e.g., wound around) the outside of sensor tube 218. In one illustrative embodiment, sensing elements 225 and 230 are resistance-thermometer elements (e.g., coils of conductive wire), but other types of sensors (e.g., resistance temperature detectors (RTD) and thermocouples) may also be utilized.

As depicted, sensing elements 225 and 230 are electrically connected to a sensing-element circuit 235. In general, the sensing-element circuit 235 is configured (responsive to signals 246, 248 from the sensing elements 225, 230, respectively) to provide an output signal 250 that is indicative of a mass flow rate of the gas stream (comprising the carrier gas 106 and the constituent vapor 204) flowing through the main path 215 of the MFC 200A. The sensing element circuit 235 may be realized by a bridge circuit such as the bridge circuit disclosed by U.S. Pat. No. 7,651,263, entitled Method and Apparatus for Measuring the Temperature of a Gas in a Mass Flow Controller, which is incorporated herein by reference.

Also shown in FIG. 2A are the downstream pressure sensor 118 coupled to the main flow path 215 near an inlet of the mass flow controller 200A, and as shown, the downstream pressure sensor 118 provides the downstream pressure signal 117 to the constituent vapor meter 110. In turn, the constituent vapor meter 110 generates the constituent-vapor-concentration signal 120 based upon the downstream pressure signal 117, the upstream pressure signal 118 (e.g., received from the upstream pressure sensor 116 depicted in FIG. 1A), and the vaporizer-temperature signal 112 (e.g., obtained at the vaporizer 102 depicted in FIGS. 1A and 1B). Although the constituent-vapor-concentration signal 120 may be represented in a variety of forms, it is contemplated that the constituent-vapor-concentration signal 120 may be representative of a percentage of mass flow in the gas stream 108 that is made up of the constituent vapor 104.

As shown in FIG. 2A, the output signal 250 may be processed by processing portion 260 to generate a signal representative of the mass flow rate of the gas stream (that includes the carrier gas 206 and the constituent vapor 204). For example, the processing portion 260 may amplify and convert, using an analog to digital converter, the output signal 250 to a digital representation of the output signal 250. And as one of ordinary skill in the art will readily recognize, the processing portion 260 may also adjust the signal 250 (e.g., by adjusting predetermined calibration coefficients) based upon physical characteristics of the MFC 200A.

The constituent-vapor mass flow meter 122 generally operates to provide an indication of the mass flow rate of the constituent vapor 104 utilizing the mass flow rate of the gas stream 108 and the concentration of the constituent vapor 104 in the gas stream 108. As shown, the constituent-vapor mass flow rate may be reported to an operator of the system, and may also be utilized to control a mass flow rate of the constituent vapor 104. More specifically, a controller 268 may generate a control signal 271 for a control valve 272 based upon a difference between a constituent-vapor-setpoint signal 270 and the constituent-vapor mass flow rate. The constituent-vapor-setpoint signal 270 represents a constituent-vapor setpoint that an operator of the MFC 200A may set.

Figure 2B:
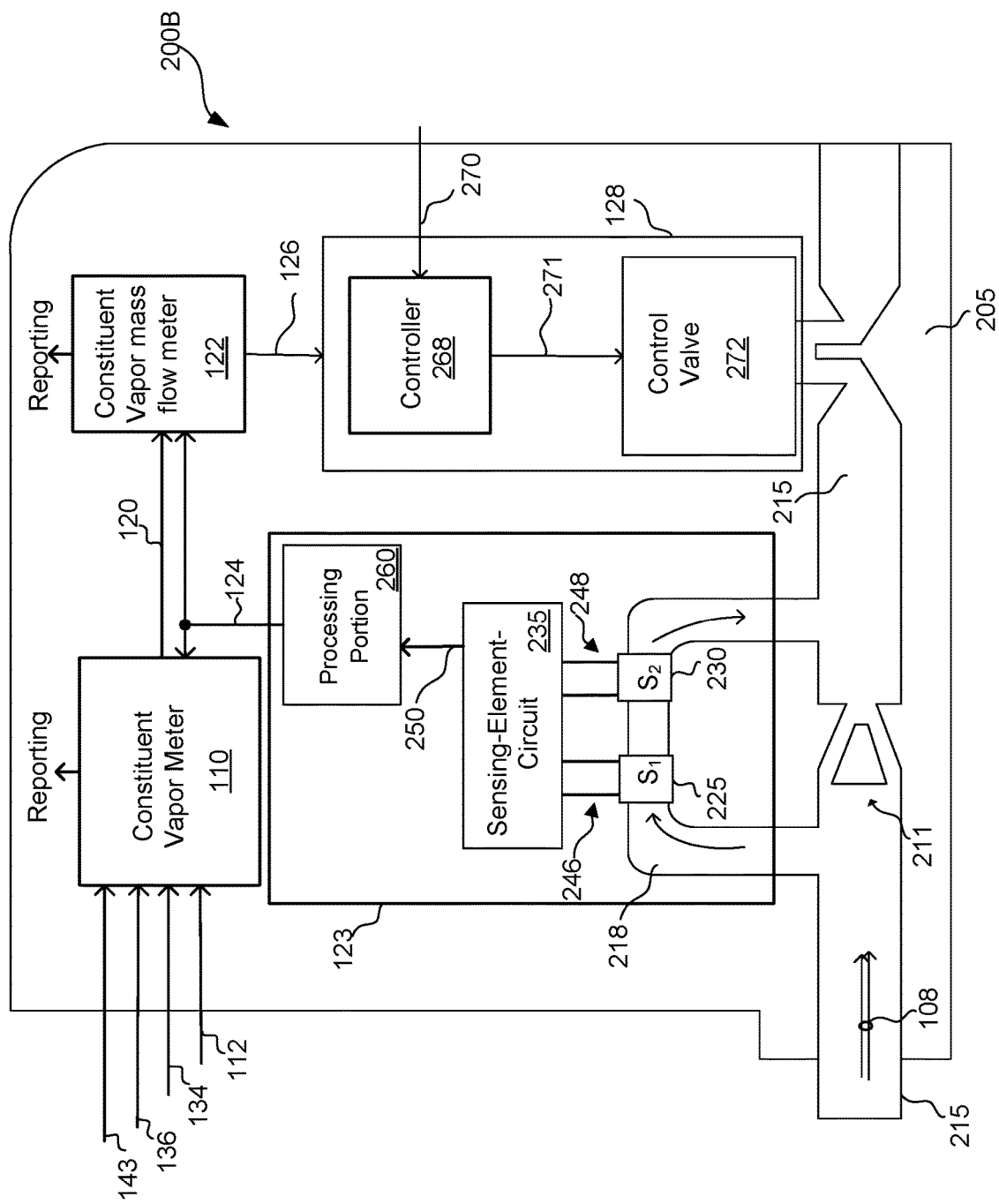
FIG. 2B is a block diagram depicting another embodiment of a mass flow controller.

Referring next to FIG. 2B, it is a functional block diagram depicting another embodiment of a mass flow controller (MFC) 200B. The embodiment depicted in FIG. 2B is very similar to the MFC 200A except the MFC 200B receives the vaporizer-pressure signal 143 indicative of the pressure of a chamber of the vaporizer 102; thus removing the need for the upstream pressure signal 115 and the downstream pressure signal 117, and removing the need for the downstream pressure sensor 118.

Figure 3:
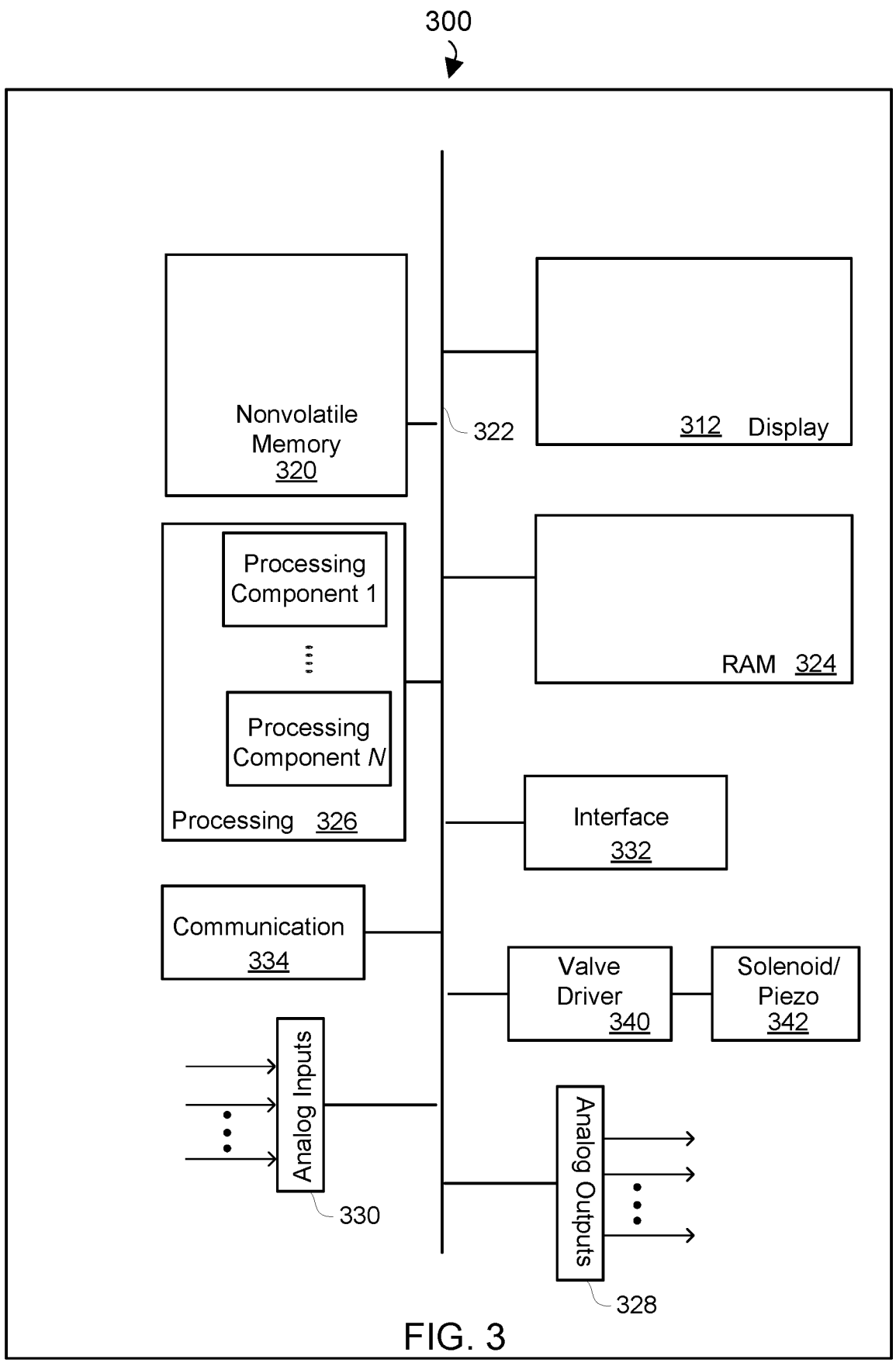
FIG. 3 is a block diagram depicting physical components of a computing device that may be used to realize aspects of the embodiments disclosed herein.

Referring next to FIG. 3, shown is a block diagram of a computing system 300 depicting physical components that may be utilized to realize aspects of the system described herein. As shown, a display portion 312 and nonvolatile memory 320 are coupled to a bus 322 that is also coupled to random access memory ("RAM") 324, a processing portion (which includes N processing components) 326, a collection of analog outputs 328, and a collection of analog inputs 330. Although the components depicted in FIG. 3 represent physical components, it should be recognized that the depicted computing system may be replicated and distributed to implement the components depicted in FIGS. 1A, 1B, 2A, and 2B.

This display portion 312 generally operates to provide a presentation of content to a user, and in several implementations, the display is realized by an LCD or OLED display. In general, the nonvolatile memory 320 functions to store (e.g., persistently store) data and executable code including non-transitory processor-executable code that is associated with the functional components depicted in FIGS. 1A, 1B, 2A, and 2B. In some embodiments for example, the nonvolatile memory 320 includes bootloader code, software, operating system code, file system code, and code to facilitate the methods described herein.

In many implementations, the nonvolatile memory 320 is realized by flash memory (e.g., NAND or ONENAND™ memory), but it is certainly contemplated that other memory types may be utilized. Although it may be possible to execute the code from the nonvolatile memory 320, the executable code in the nonvolatile memory 320 is typically loaded into RAM 324 and executed by one or more of the N processing components in the processing portion 326.

The N processing components in connection with RAM 324 generally operate to execute the instructions stored in nonvolatile memory 320 to effectuate functional components depicted in FIGS. 1A, 1B, 2A, and 2B. For example, the constituent vapor meter 110, constituent-vapor mass flow meter 122, controller 268, and other logical aspects of mass flow controllers and mass flow meters described herein may be realized by one or more of the N processing components in connection with non-transitory processor-readable code that is executed from RAM 324.

The interface component 332 generally represents one or more components that enable a user and devices to interact with the systems described herein. The interface component 332, for example, may include a keypad, touch screen, digital inputs, and one or more analog or digital controls, and the interface component 332 may be used to translate an input from a user into the mass flow set point signal. In the event one or more signals disclosed herein (e.g., the upstream pressure signal 115, downstream pressure signal 117, and vaporizer-temperature signal 112) are digital signals, the interface component 332 may receive and propagate the digital signals to the bus 322.

A communication component 334 generally enables one or more components of the systems disclosed herein to communicate with external networks and devices including external processing components (e.g., plasma processing components). One of ordinary skill in the art will appreciate that the communication component 334 may include components (e.g., that are integrated or distributed) to enable a variety of wireless (e.g., WiFi) and wired (e.g., Ethernet) communications.

Analog inputs 330 may include the upstream pressure signal 115 as an analog signal indicative of the upstream pressure (from the upstream pressure sensor 116), the downstream pressure signal 117 as an analog signal indicative of the downstream pressure (from the downstream pressure sensor 118) and the vaporizer-temperature signal 112 as an analog input indicative of the temperature (e.g., from the temperature sensor 114 coupled to the vaporizer 102). Also shown in FIG. 3 are a valve driver 340 and a solenoid/piezo portion 342. The solenoid/piezo portion 342 generally represents technology used in the control valve 272 depicted in FIGS. 2A and 2B, which may be a solenoid-type valve or a piezo-type valve. The valve driver 340 may generate and provide a current or voltage to the solenoid/piezo portion 342 to control the position of the control valve 272.

Figure 4:
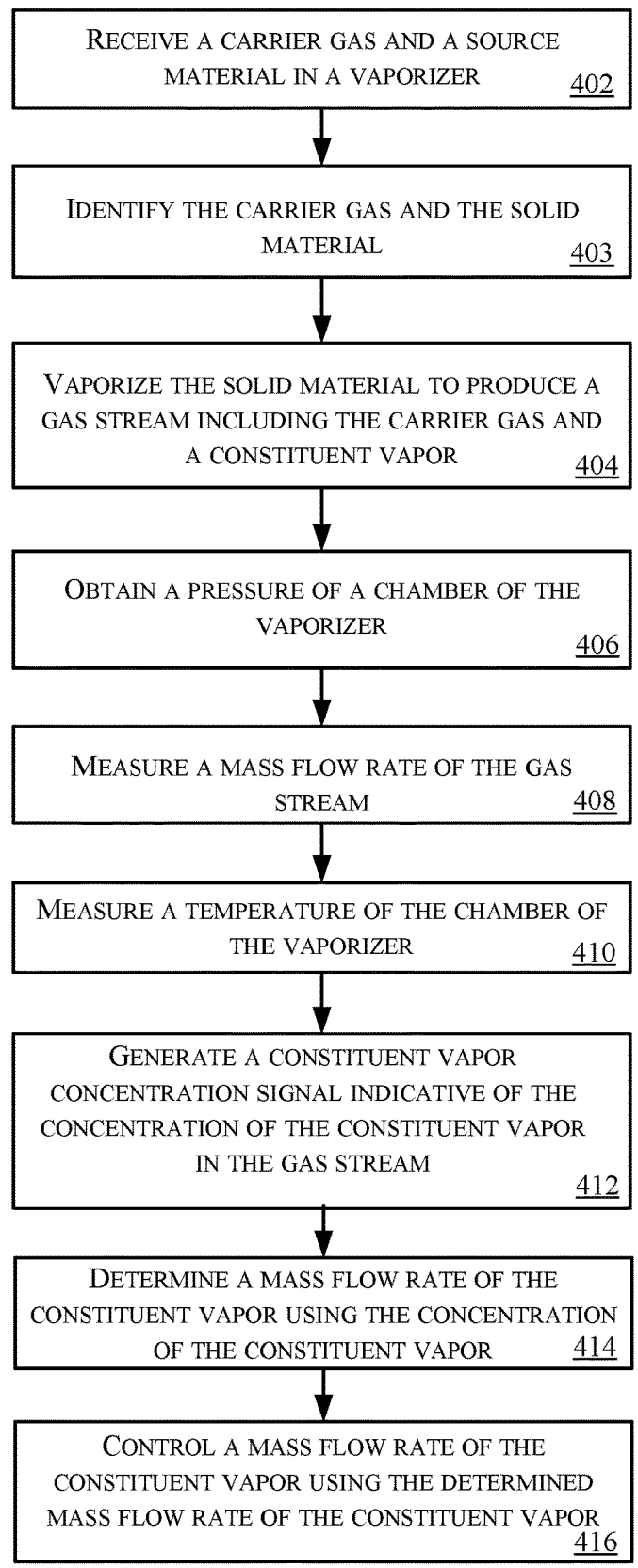
FIG. 4 is a flowchart depicting a method that may be traversed in connection with embodiments disclosed herein.

Referring next to FIG. 4, shown is a flowchart depicting a method that may be traversed in connection with embodiments disclosed herein. As shown, the vaporizer 102 receives the carrier gas 108 and a source material 103 (Block 402), and the carrier gas 108 and the source material 103 are identified (Block 403). As discussed above and below, an awareness of the types of gases that are utilized (in connection with other measured parameter values discussed above and below) enables a calculation of the concentration of the constituent gas 104 in the gas stream.

As shown, the source material 103 is vaporized in the vaporizer 102 to produce a gas stream 108 including the carrier gas 106 and the constituent vapor 104 (Block 404). Then, a pressure of a chamber of the vaporizer 102 is obtained (Block 406). As discussed above, the pressure of the chamber of the vaporizer 102 may be obtained by direct measurement of the pressure by the vaporizer-pressure sensor 142, or by calculating the pressure of the chamber of the vaporizer 102 using the upstream pressure sensor 116 and the downstream pressure sensor 118.

In addition, a mass flow rate of the gas stream 108 is measured (Block 408), and a temperature of the chamber of the vaporizer 102 is measured (Block 410). The constituent-vapor-concentration signal 120 indicative of the concentration the constituent vapor 104 in the gas stream 108 is then generated (Block 412).

The concentration the constituent vapor 104 in the gas stream 108 is dependent on the following parameters: i) chemical properties of the carrier gas 106 (e.g., saturation and ability to carry the constituent vapor 104); ii) chemical properties of the constituent vapor 104 (e.g., heat capacity); iii) the mass flow rate of the gas stream 108, which may be used to determine a speed of the gas stream 108 through the vaporizer 102 (a concentration of the constituent gas is inversely proportional to the gas speed); and iv) a rate of vaporization. A concentration of the constituent vapor 104 is directly proportional to the rate of vaporization of the source material 103.

Both a temperature of the chamber of the vaporizer 102 and a pressure of the chamber of the vaporizer 102 affect the rate of vaporization of the source material 103. In particular, the rate of vaporization of the source material 103 is directly proportional to temperature and inversely proportional to pressure. As discussed above, the pressure of the chamber of the vaporizer 102 may not be directly available, but the pressure of the chamber of the vaporizer 102 can be calculated using the upstream pressure signal 115, the downstream pressure signal 117, and the measurement of the mass flow of the gas stream 108.

As shown in FIG. 4, the mass flow rate of the constituent vapor 104 may be determined using the concentration of the constituent vapor (Block 414). For example, the determination of the mass flow rate of the constituent vapor 104 may include multiplying a concentration of the constituent vapor 104 (represented as a percent of the mass flow rate of the gas stream 108) by the mass flow rate of the gas stream 108. The mass flow rate of the constituent vapor 104 may then be controlled using the determined mass flow rate of the constituent vapor (Block 416). The controller 268, for example, may adjust the control valve 272 until a mass flow rate of the constituent vapor 104 is equal to the constituent-vapor-setpoint signal 270. As one of ordinary skill in the art will appreciate, non-transitory processor-readable code may be encoded with instructions to execute aspects of the method.

In conclusion, aspects disclosed herein provide, among other things, a system and method for determining and reporting a concentration of a constituent vapor 104 in a gas stream 108. In some embodiments, the determined concentration of the constituent vapor 104 may be used to control a mass flow rate of the constituent vapor 104. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed herein.

What is claimed is:

1. A mass flow control system comprising:
a vaporizer disposed to receive a carrier gas and a source material to be vaporized, wherein the vaporizer is configured to vaporize the source material to provide a constituent vapor along with the carrier gas as a gas stream;
means for obtaining a pressure of a chamber of the vaporizer;
a mass flow meter coupled to the output of the vaporizer, wherein the mass flow meter is configured to provide a gas-stream-flow-rate signal indicative of a mass flow rate of the gas stream;
a temperature sensor thermally coupled to the vaporizer, wherein the temperature sensor is configured to provide a vaporizer-temperature signal indicative of a temperature of the chamber of the vaporizer;
a constituent vapor meter configured to provide a constituent-vapor-concentration signal using the pressure of the chamber of the vaporizer, the gas-stream-flow-rate signal, the vaporizer-temperature signal, and information about the carrier gas and the constituent vapor, wherein the constituent-vapor-concentration signal is indicative of a concentration of the constituent vapor in the gas stream;
a constituent-vapor mass flow meter configured to provide a constituent-vapor-mass-flow-rate signal by multiplying the concentration of the constituent vapor in the gas stream by the mass flow rate of the gas stream, wherein the constituent-vapor-mass-flow-rate signal is indicative of a mass flow rate of the constituent vapor; and
a mass flow control module configured to receive the constituent-vapor-mass-flow-rate signal and a single constituent-vapor-setpoint signal set by an operator of the mass flow control system that represents a constituent-vapor-setpoint, and the mass flow control module is configured to adjust a mass flow rate of the gas stream until the mass flow rate of the constituent vapor equals the constituent-vapor-setpoint and maintain the mass flow rate of the constituent vapor at the constituent-vapor-setpoint while enabling the mass flow rate of the gas stream, the temperature of the chamber and the pressure of the chamber to vary, wherein the constituent-vapor-setpoint is a desired mass flow rate of the constituent vapor.

2. A mass flow control system of claim 1, wherein the means for obtaining the pressure of the chamber of the vaporizer includes:
a vaporizer-pressure sensor coupled to the vaporizer, wherein the vaporizer-pressure sensor is configured to sense a pressure of a chamber of the vaporizer and provide a vaporizer-pressure signal indicative of the pressure of a chamber of the vaporizer;
wherein the constituent vapor meter is configured to obtain the pressure of the chamber of the vaporizer from the vaporizer-pressure sensor.

3. The mass flow control system of claim 1, wherein the means for obtaining the pressure of the chamber of the vaporizer includes:
an upstream pressure sensor coupled to an input of the vaporizer, wherein the upstream pressure sensor is configured to sense a pressure of the carrier gas and provide an upstream pressure signal; and
a downstream pressure sensor coupled to an output of the vaporizer, wherein the downstream pressure sensor is configured to sense a pressure of the gas stream at an output of the vaporizer and provide a downstream pressure signal;
wherein the constituent vapor meter is configured to calculate the pressure of the chamber of the vaporizer from the upstream pressure signal and the downstream pressure signal.

4. A mass flow controller, comprising:
a conduit to receive a gas stream including a carrier gas and a constituent vapor;
a mass flow meter disposed to receive the gas stream from the conduit, wherein the mass flow meter is configured to provide a gas-stream-flow-rate signal indicative of a mass flow rate of the gas stream;
a constituent vapor meter configured to provide a constituent-vapor-concentration signal using a pressure of a chamber of a vaporizer, the gas-stream-flow-rate signal, a vaporizer-temperature signal, and information about the carrier gas and the constituent vapor, wherein the constituent-vapor-concentration signal is indicative of a concentration of the constituent vapor in the gas stream;
a constituent-vapor mass flow meter configured to provide a constituent-vapor-mass-flow-rate signal by multiplying the concentration of the constituent vapor in the gas stream by the mass flow rate of the gas stream, wherein the constituent-vapor-mass-flow-rate signal is indicative of a mass flow rate of the constituent vapor;
a control valve coupled to the conduit to control a mass flow rate of the gas stream; and
a controller disposed to receive a single constituent-vapor-setpoint signal set by an operator of the mass flow controller and the constituent-vapor-mass-flow-rate signal and adjust the control valve so the constituent-vapor-mass-flow-rate signal equals the single constituent-vapor-setpoint signal while enabling the mass flow rate of the gas stream, the temperature of the chamber and the pressure of the chamber to vary, wherein the constituent-vapor-setpoint is a desired mass flow rate of the constituent vapor.

5. A mass flow controller of claim 4 wherein the constituent vapor meter is configured to obtain the pressure of the chamber of the vaporizer from a vaporizer-pressure signal obtained from a vaporizer-pressure sensor coupled to the vaporizer.

6. The mass flow control system of claim 4, wherein the constituent vapor meter is configured to receive an upstream pressure signal and a downstream pressure signal and calculate the pressure of a chamber of the vaporizer from the upstream pressure signal and the downstream pressure signal.

* * * * *